United States Patent
Nandy et al.

(10) Patent No.: US 10,640,446 B2
(45) Date of Patent: May 5, 2020

(54) SYNTHESIS OF ALKYL TRIBENZANOATE

(71) Applicant: SABIC GLOBAL TECHNOLOGIES B.V., Bergen op Zoom (NL)

(72) Inventors: Ritesh Nandy, Bangalore (IN); Vishal Patrick, Bangalore (IN); Edward Joseph Nesakumar, Bangalore (IN)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 16/302,446

(22) PCT Filed: May 23, 2017

(86) PCT No.: PCT/IB2017/053042
§ 371 (c)(1),
(2) Date: Nov. 16, 2018

(87) PCT Pub. No.: WO2017/203434
PCT Pub. Date: Nov. 30, 2017

(65) Prior Publication Data
US 2019/0292126 A1    Sep. 26, 2019

Related U.S. Application Data

(60) Provisional application No. 62/341,145, filed on May 25, 2016.

(51) Int. Cl.
*C07C 67/08* (2006.01)
*C07C 63/331* (2006.01)

(52) U.S. Cl.
CPC .......... *C07C 67/08* (2013.01); *C07C 63/331* (2013.01)

(58) Field of Classification Search
CPC ........ C07C 67/08; C07C 67/54; C07C 63/331
See application file for complete search history.

(56) References Cited

U.S. PATENT DOCUMENTS

| | | | |
|---|---|---|---|
| 3,736,348 A | 5/1973 | Gouth et al. | |
| 4,007,218 A * | 2/1977 | Ghanayem | C07C 69/44 560/99 |
| 4,284,793 A * | 8/1981 | Sagara | C07C 67/60 560/78 |
| 5,434,294 A | 7/1995 | Pugach et al. | |
| 7,632,961 B2 | 12/2009 | Brueschken et al. | |
| 2015/0344400 A1 * | 12/2015 | Frey | C07C 67/08 560/200 |

FOREIGN PATENT DOCUMENTS

| | | | |
|---|---|---|---|
| CN | 100363328 C | 1/2008 | |
| CN | 101429126 A | 5/2009 | |
| CN | 101590402 A | 12/2009 | |
| CN | 102030652 A | 4/2011 | |
| CN | 102924280 A | 2/2013 | |
| CN | 103007920 A | 4/2013 | |
| CN | 103304419 A | 9/2013 | |
| GB | 1426057 * | 2/1976 | ............. C07C 67/76 |
| GB | 1426057 A | 2/1976 | |
| JP | 61068448 A | 4/1986 | |
| JP | 2004120123 A | 4/2004 | |
| JP | 2005213189 A | 8/2005 | |
| JP | 2012092074 A | 5/2012 | |

OTHER PUBLICATIONS

International Search Report for International Application No. PCT/IB2017/053042, International Filing Date May 23, 2017, dated Sep. 13, 2017, 5 pages.
Jiang et al.; Study on the Synthesis of Tri(2-ethylhexyl) trimellitate; vol. 60; Iss 6; 2002, 4 pages; with English abstract.
Written Opinion for International Application No. PCT/IB2017/053042, International Filing Date May 23, 2017, dated Sep. 13, 2017, 5 pages.
Zhao, J., Synthesis of Tri(2-ethylhexyl) Trimellitate from Trimellitic Anhydride and 2-ethylhexanol by esterification with nonacid catalyst; vol. 22 Iss 7; 1993, English Abstract Only, 1 page.
International Search Report for International Application No. PCT/IB2019/054826; International Filing Date Jun. 10, 2019; dated Sep. 27, 2019; 5 pages.
Written Opinion for International Application No. PCT/IB2019/054826; International Filing Date Jun. 10, 2019; dated Sep. 27, 2019; 7 pages.

* cited by examiner

*Primary Examiner* — Yate K Cutliff
(74) *Attorney, Agent, or Firm* — Cantor Colburn LLP

(57) ABSTRACT

A method of making alkyl tribenzanoates includes combining a phenyl tricarboxylic acid or chemical equivalent thereof with greater than or equal to 3.5 molar equivalents of a $C_4$-$C_{18}$ alkyl alcohol, based on the amount of phenyl tricarboxylic acid or chemical equivalent thereof, in the presence of 0.05 to 0.20 mol % of a titanium tetra-alkoxide catalyst, based on the total moles of phenyl tricarboxylic acid or chemical equivalent, at a temperature greater than 210° C. to form a reaction mixture having an acid value less than or equal to 0.5 as determined according to ASTM D1045.

20 Claims, No Drawings

SYNTHESIS OF ALKYL TRIBENZANOATE

CROSS REFERENCE TO RELATED APPLICATIONS

This application is a National Stage application of PCT/IB2017/053042, filed May 23, 2017, which claims the benefit of U.S. Provisional Application No. 62/341,145, filed May 25, 2016, both of which are incorporated by reference in their entirety herein.

BACKGROUND

Plasticizers are widely used in many polymer compositions, coating compositions, sealing compositions and rubber compositions. Dioctylterephthalate has been widely used in the past but is being phased out. Alkyl tribenzanoates are being considered as replacement plasticizers for dioctylterephthalate and related compounds. A process for synthesizing alkyl tribenzanoates which is similar to the current synthetic methods for dioctylterephthalate would take advantage of current commercial infrastructure.

BRIEF DESCRIPTION

A method of making alkyl tribenzanoates comprises combining a phenyl tricarboxylic acid or chemical equivalent thereof with greater than or equal to 3.5 molar equivalents of a $C_4$-$C_{18}$ alkyl alcohol in the presence of 0.05 to 0.20 mol % of a titanium tetra-alkoxide catalyst, based on the total moles of phenyl tricarboxylic acid or chemical equivalent, at a temperature greater than 210° C. to form a reaction mixture having an acid value less than or equal to 0.5 as determined according to ASTM D1045.

The aforementioned method can further comprise neutralizing the reaction mixture with an aqueous caustic solution, purging the neutralized reaction mixture with carbon dioxide, distilling any residual $C_4$-$C_{18}$ alkanol from the purged reaction mixture, filtering the distilled reaction mixture through celite, and contacting the filtered reaction mixture with charcoal. After removing the charcoal the product has an acid value less than 0.1 and an APHA color value less than 30 wherein both are determined according to ASTM D1045.

In some embodiments the method comprises combining a trimellitic acid, trimellitic anhydride or a combination thereof with greater than or equal to 3.5 molar equivalents of 2-ethylhexyl alcohol, based on the total moles of trimellitic acid and trimellitic anhydride, in the presence of 0.05 to 0.20 mol % of a titanium tetra-isopropoxide catalyst at a temperature greater than 210° C. to form a reaction mixture having an acid value less than or equal to 0.5 as determined according to ASTM D1045.

The above described and other features are exemplified by the detailed description.

DETAILED DESCRIPTION

Alkyl tribenzanoates offer an alternative to dialkyl phthalate plasticizers. By making alkyl tribenzaotes in a manner similar to the method for making dialkyl phthalates, both types of plasticizers can be made in the same facility or the facility can be readily converted to the manufacture of alkyl tribenzanoates. While similar in structure to dialkyl phthalates, the synthesis of alkyl tribenzanoates offers some unique challenges such as triesterification and a greater viscosity of the reagent and the product compound. Triesterification offers more opportunities for an incomplete reaction and side products compared to diesterification and hence more difficulties in obtaining a high purity product after isolation. Furthermore, the increased viscosity of the trialkyl benzanoate compared to the dialkyl phthalate can hamper isolation efforts.

A method of making alkyl tribenzanoates comprises combining a phenyl tricarboxylic acid or chemical equivalent thereof with greater than or equal to 3.5 molar equivalents of a $C_4$-$C_{18}$ alkyl alcohol in the presence of 0.05 to 0.20 mol % of a titanium tetra-alkoxide catalyst at a temperature greater than 210° C. to form a reaction mixture having an acid value less than or equal to 0.5. In some embodiments the acid value is less than 0.3. The method can further comprise neutralizing the reaction mixture with an aqueous caustic solution and purging the neutralized reaction mixture with carbon dioxide, distilling any residual $C_1$-$C_{10}$ alkanol from the purged reaction mixture, filtering the distilled reaction mixture through celite, and contacting the filtered reaction mixture with charcoal. After removal of the charcoal, the product has an acid value less than or equal to 0.1 and an APHA color value less than or equal to 30 as measured by ASTM D1045.

Phenyl tricarboxylic acid has the formula (1):

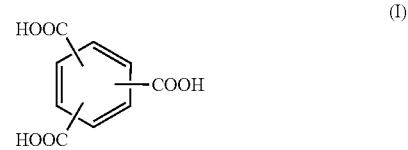

Chemical equivalents of phenyl tricarboxylic acid include compounds in which two of the carboxylic acid groups are located at adjacent carbons and together form an anhydride. An exemplary anhydride is trimellitic anhydride as show in Formula II

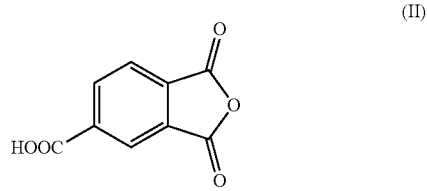 [SMILES: O=C(O)c1ccc2c(c1)C(=O)OC2=O]

The $C_4$-$C_{18}$ alkyl alcohol is saturated, unsubstituted and can be straight chain or branched. Exemplary alcohols include n-butanol, octanol, isononanol, isodecanol, decanol, and 2-ethylhexyl alcohol. In some embodiments the $C_4$-$C_{18}$ alkyl alcohol comprises 2-ethylhexyl alcohol. The $C_4$-$C_{18}$ alkyl alcohol is present in the reaction in an amount greater than or equal to 3.5 molar equivalents based on the amount of the phenyl tricarboxylic acid or chemical equivalent thereof. In some embodiments the $C_4$-$C_{18}$ alkyl alcohol is present in an amount of 3.5 to 4.5 molar equivalents, or, more specifically, in an amount of 3.5 to 4.0 molar equivalents.

The titanium tetra-alkoxide catalyst comprises four alkoxide ligands, each having 1 to 18 carbons. It is contemplated that the titanium tetra-alkoxide can comprise a mixture of alkoxide ligands having a different number of carbons, the four alkoxide ligands can all have the same number of carbons but be different isomers or the four alkoxide ligands can have the same number of carbons and the same structure. Exemplary titanium tetra-alkoxide catalysts include titanium tetra-isopropoxide, titanium tetra-butoxide, and combinations of the foregoing. The titanium tetra-alkoxide can be present in an amount of 0.05 to 0.20 mol %, or, 0.11 to 0.16 mol %, based on the total moles phenyl tricarboxylic acid or chemical equivalent thereof.

Temperature of the reaction is greater than 210° C. In some embodiments the temperature of the reaction is less than or equal to 250° C. Within this range the temperature can be 210 to 240° C., or, 220 to 235° C., or 225 to 230° C.

The time for the reaction can be 1 to 7 hours, or, 2 to 6 hours, or, more specifically, 3 to 5 hours. When the reaction mixture has an acid value less than 0.5 as determined according to ASTM D1045 the reaction is deemed complete.

After the reaction is complete the product alkyl tribenzanoate is isolated from the remainder of the reaction mixture. Isolation comprises removal of the excess $C_4$-$C_{18}$ alkyl alcohol. The excess $C_4$-$C_{18}$ alkyl alcohol can be removed by distillation under reduced pressure. For example, when the alcohol is 2-ethylhexyl alcohol distillation can occur at temperatures of 135 to 230° C. and a pressure of 7 to 8 millibars.

After removal of the excess $C_4$-$C_{18}$ alkyl alcohol the temperature of the distilled mixture is reduced to less than 100° C. and an aqueous caustic solution is introduced to neutralize the reaction mixture. It is also contemplated that the reaction mixture can be neutralized prior to removal of any excess $C_4$-$C_{18}$ alkyl alcohol. The aqueous caustic solution comprises a base such as sodium hydroxide, potassium hydroxide or the like. The amount of aqueous caustic solution added to the reaction mixture is chosen to provide an amount of base which is equivalent to or a slight excess to the amount of acid in the reaction mixture. Exemplary amounts are 1 to 3 weight percent, based on the amount of phenyl tricarboxylic acid or chemical equivalent added to the reaction, of caustic solution having a concentration of about 40 to 60 weight percent caustic, based on the total weight of the caustic solution. Neutralization typically proceeds for 30 to 40 minutes and the neutralized mixture can become milky or cloudy. The neutralized reaction mixture is purged with carbon dioxide to neutralize excess caustic. Purging can occur over a time period of 10 to 60 minutes, or 15 to 45 minutes, or, more specifically, 20 to 30 minutes. The purged mixture is distilled to remove water, typically at a temperature of 40 to 50° C. and reduced pressure such as 7-8 millibar. After the water is removed the temperature of the mixture can be increased to remove any residual $C_4$-$C_{18}$ alkyl alcohol while maintaining the mixture at a reduced pressure. The mixture can then be cooled to a temperature of 100 to 140° C., or, more specifically, 110 to 130° C. and filtered, typically through celite. The filtered liquid is treated with charcoal for 25 to 45 minutes, or, 30 to 40 minutes at a temperature of 50 to 70° C., or, 55 to 65° C. After the charcoal treatment the mixture is filtered again over celite at a temperature of 90 to 110° C. due to the viscosity of the product material. The amount of celite and charcoal used in the foregoing isolation steps can be 0.5 to 2 weight percent, based on the weight of the phenyl tricarboxylic acid or chemical equivalent used in the reaction. The final product has an acid value less than or equal to 0.1 and an APHA color value less than 30 as determined by ASTM D1045.

This disclosure is further illustrated by the following examples, which are non-limiting.

EXAMPLES

The examples were performed using the following basic procedure. A four neck round bottom flask was equipped with a magnetic stirrer, an oil bath, a Dean-Stark apparatus and a thermometer. 100 grams of trimellitic anhydride (TMA) was added to the flask with the specified amount of 2-ethylhexyl alcohol. The mixture was stirred and heated over an oil bath with a temperature of 210-230° C. The reaction mixture became transparent when the reaction mixture reached a temperature of approximately 150° C. The catalyst (titanium tetra-isopropoxide) was added when the reaction mixture had a temperature of approximately 170° C. After catalyst addition immediate formation of water was observed. The water formed during the reaction was collected in the Dean-Stark apparatus. The Dean-Stark apparatus was drained of water periodically and the 2-ethylhexyl alcohol collected in the apparatus was returned to the reaction mixture. After 4-6 hours the acid value of the reaction mixture was below 0.5. The reaction mixture was cooled to a temperature less than 100° C. and prepared for distillation under vacuum. After setting the vacuum pressure to 7-8 millibar the reaction mixture temperature was slowly raised to 230° C. to remove most of the 2-ethyhexyl alcohol. The temperature of the reaction mixture was then reduced to approximately 90° C. and 3 milliliters of a caustic solution (49 weight percent of NaOH in water) was added and stirred for 30-40 minutes. The reaction was purged with carbon dioxide for 20-30 minutes and the mixture was distilled again under reduced pressure to remove water and remaining 2-ethylhexyl alcohol. The temperature of the mixture was reduced to approximately 120° C. and then filtered over 1 gram of celite to remove a white solid and obtain a viscous liquid. The liquid was then contacted with 1 gram of charcoal at about 100° C. and filtered over 1 gram of celite. The resulting product was tested for purity by gas chromatography (GC), refractive index, color, acid value and specific gravity.

Examples 1-3

The amount of 2-ethylhexyl alcohol (2-EH) was varied. The reaction and isolation was performed as described above using a temperature of 210-230° C. and 90-120° C. respectively. Results are shown in Table 1. The amounts of 2-ethylhexyl alcohol are molar equivalents based on the amount of trimellitic anhydride. The amount of catalyst was 0.11 mol % based on the amount of trimellitic anhydride. Prior to isolation the amount of product was estimated by GC/MS.

TABLE 1

| | | | Before isolation | | After isolation | | |
|---|---|---|---|---|---|---|---|
| | 2-EH | Conversion of TMA | Acid value | Estimated product | Acid value | Wt % of product | APHA |
| 1* | 3.25 equivalents | 100% | 9 | 91.9 | ** | ** | ** |
| 2 | 3.5 equivalents | 100% | 0.1 | 97.3 | 0.07 | 97.6 | 23 |
| 3 | 3.75 equivalents | 100% | 0.12 | 97.2 | 0.05 | 97.5 | 13 |

*Comparative Example
** Not available. Isolation was not performed because the reaction was slow and there was low selectivity for the product.

The results in Table 1 show that the amount of the alcohol in the reaction needs to be 3.5 molar equivalents or greater. At 3.75 molar equivalents there was lower color in the isolated product.

Examples 4-6

The amount of catalyst was varied in these examples. The amount of catalyst is in mol % based on the amount of trimellitic anhydride. The reaction, testing and isolation were performed as described above in the general procedure and in Examples 1-3 using 3.75 molar equivalents of 2-ethylhexyl alcohol. Results are shown in Table 2.

TABLE 2

| | | | Before isolation | | After isolation | | |
|---|---|---|---|---|---|---|---|
| | Catalyst | Conversion of TMA | Acid value | Estimated product | Acid value | Wt % of product | APHA |
| 4 | 0.11 mol % | 100% | 0.12 | 97.2 | 0.05 | 97.5 | 13 |
| 5 | 0.16 mol % | 100% | 0.25 | 97.3 | 0.05 | 97.8 | 27 |
| 6* | 0.22 mol % | 100% | 0.47 | 97.2 | 0.06 | 97.8 | 39 |

*Comparative example

A comparison of the APHA color values of the examples after isolation shows that the amount of catalyst has an effect on the color of the isolated product. The amount of catalyst must kept below 0.20 mol % in order to obtain a color value less than or equal to 30 after isolation.

Examples 7-8

The reaction temperature was varied to see the effect on the reaction. The reaction was run as described above using 3.75 molar equivalent of 2-ethylhexyl alcohol and 0.11 mol % of catalyst. At 210° C. the reaction was slow and the reaction was not complete after 8 hours. The product was not isolated. In contrast, at 230° C. the reaction was complete in 4 hours.

This disclosure further encompasses the following embodiments.

Embodiment 1

A method of making alkyl tribenzanoates comprising: combining a phenyl tricarboxylic acid or chemical equivalent thereof with greater than or equal to 3.5 molar equivalents of a $C_4$-$C_{18}$ alkyl alcohol, based on the amount of phenyl tricarboxylic acid or chemical equivalent thereof, in the presence of 0.05 to 0.20 mol % of a titanium tetra-alkoxide catalyst, based on the total moles of phenyl tricarboxylic acid or chemical equivalent, at a temperature greater than 210° C. to form a reaction mixture having an acid value less than or equal to 0.5 as determined according to ASTM D1045.

Embodiment 2

The method of Embodiment 1 further comprising neutralizing the reaction mixture with an aqueous caustic solution, and purging the neutralized reaction mixture with carbon dioxide.

Embodiment 3

The method of Embodiment 1 or 2, further comprising distilling any residual $C_4$-$C_{18}$ alkanol from the reaction mixture either prior to purging, subsequent to purging or both.

Embodiment 4

The method of Embodiment 3, further comprising filtering the distilled reaction mixture after purging through celite, contacting the filtered reaction mixture with charcoal; and filtering the charcoal containing mixture to produce a product having an acid value less than 0.1 and an APHA color value less than 30 as determined according to ASTM D1045.

Embodiment 5

The method of any of the preceding Embodiments, wherein the phenyl tricarboxylic acid or chemical equivalent thereof comprises trimellitic anhydride.

Embodiment 6

The method of any of the preceding Embodiments wherein the $C_4$-$C_{18}$ alkyl alcohol comprises 2-ethylhexyl alcohol.

Embodiment 7

The method of any of the preceding Embodiments wherein the titanium tetra-alkoxide catalyst comprises titanium tetra-isopropoxide catalyst.

Embodiment 8

The method of any of the preceding Embodiments wherein the reaction mixture has an acid value less than or equal to 0.3.

Embodiment 9

The method of any of the preceding Embodiments wherein the $C_4$-$C_{18}$ alkyl alcohol is present in an amount of 3.5 to 4.5 molar equivalents, based on the amount of phenyl tricarboxylic acid or chemical equivalent thereof.

Embodiment 10

The method of any of the preceding Embodiments wherein the temperature is less than or equal to 250° C.

Embodiment 11

A method of making alkyl tribenzanoates comprising: combining a phenyl tricarboxylic acid or chemical equivalent thereof with greater than or equal to 3.5 molar equivalents of a $C_4$-$C_{18}$ alkyl alcohol in the presence of 0.05 to 0.20 mol % of a titanium tetra-isopropoxide, based on the total moles of phenyl tricarboxylic acid or chemical equivalent, at a temperature greater than 210° C. to form a reaction mixture; neutralizing the reaction mixture with an aqueous caustic solution and purging the neutralized reaction mixture with carbon dioxide; distilling any residual $C_4$-$C_{18}$ alkanol from the purged reaction mixture; filtering the distilled reaction mixture through celite; and contacting the filtered reaction mixture with charcoal to form a product having an acid value less than 0.1 and an APHA color value less than or equal to 30 both determined according to ASTM D1045.

Embodiment 12

The method of Embodiment 11, further comprising distilling $C_4$-$C_{18}$ alkanol from the reaction mixture prior to neutralizing.

Embodiment 13

The method of Embodiment 11 or 12, wherein the phenyl tricarboxylic acid or chemical equivalent thereof comprises trimellitic anhydride.

Embodiment 14

The method of any of Embodiments 11 to 13, wherein the $C_4$-$C_{18}$ alkyl alcohol comprises 2-ethylhexyl alcohol.

Embodiment 15

A method of making alkyl tribenzanoates comprising combining a trimellitic acid, trimellitic anhydride or combination thereof with greater than or equal to 3.5 molar equivalents of a 2-ethylhexyl alcohol, based on the total moles of trimellitic acid or trimellitic anhydride, in the presence of 0.05 to 0.20 mol % of a titanium tetra-isopropoxide catalyst at a temperature greater than 210° C. to form a reaction mixture having an acid value less than or equal to 0.3.

Embodiment 16

The method of Embodiment 15 further comprising neutralizing the reaction mixture with an aqueous caustic solution, and purging the neutralized reaction mixture with carbon dioxide.

Embodiment 17

The method of Embodiment 15 or 16, further comprising distilling any residual $C_4$-$C_{18}$ alkanol from the reaction mixture either prior to purging, subsequent to purging or both.

Embodiment 18

The method of Embodiment 17, further comprising filtering the distilled reaction mixture after purging through celite, contacting the filtered reaction mixture with charcoal; and filtering the charcoal containing mixture to produce a product having an acid value less than 0.1 and an APHA color value less than 30 as determined according to ASTM D1045.

Embodiment 19

The method of any of Embodiments 15 to 18, wherein the 2-ethylhexyl alcohol is present in an amount of 3.5 to 4.5 molar equivalents, based on the total moles of trimellitic acid or trimellitic anhydride.

Embodiment 20

The method of any of Embodiments 15 to 19, wherein the temperature is less than or equal to 250° C.

The compositions, methods, and articles can alternatively comprise, consist of, or consist essentially of, any appropriate materials, steps, or components herein disclosed. The compositions, methods, and articles can additionally, or alternatively, be formulated so as to be devoid, or substantially free, of any materials (or species), steps, or components, that are otherwise not necessary to the achievement of the function or objectives of the compositions, methods, and articles.

All ranges disclosed herein are inclusive of the endpoints, and the endpoints are independently combinable with each other (e.g., ranges of "up to 25 wt. %, or, more specifically, 5 wt. % to 20 wt. %", is inclusive of the endpoints and all intermediate values of the ranges of "5 wt. % to 25 wt. %," etc.). "Combinations" is inclusive of blends, mixtures, alloys, reaction products, and the like. The terms "first," "second," and the like, do not denote any order, quantity, or importance, but rather are used to distinguish one element from another. The terms "a" and "an" and "the" do not denote a limitation of quantity, and are to be construed to cover both the singular and the plural, unless otherwise indicated herein or clearly contradicted by context. "Or" means "and/or" unless clearly stated otherwise. Reference throughout the specification to "some embodiments", "an embodiment", and so forth, means that a particular element described in connection with the embodiment is included in at least one embodiment described herein, and may or may not be present in other embodiments. In addition, it is to be understood that the described elements may be combined in any suitable manner in the various embodiments.

Unless specified to the contrary herein, all test standards are the most recent standard in effect as of the filing date of this application, or, if priority is claimed, the filing date of the earliest priority application in which the test standard appears.

Unless defined otherwise, technical and scientific terms used herein have the same meaning as is commonly understood by one of skill in the art to which this application belongs. All cited patents, patent applications, and other references are incorporated herein by reference in their entirety. However, if a term in the present application contradicts or conflicts with a term in the incorporated reference, the term from the present application takes precedence over the conflicting term from the incorporated reference.

Compounds are described using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, —CHO is attached through carbon of the carbonyl group.

The term "alkyl" means a branched or straight chain, unsaturated aliphatic hydrocarbon group, e.g., methyl, ethyl, n-propyl, i-propyl, n-butyl, s-butyl, t-butyl, n-pentyl, s-pentyl, and n- and s-hexyl. "Alkenyl" means a straight or branched chain, monovalent hydrocarbon group having at least one carbon-carbon double bond (e.g., ethenyl (—HC=CH$_2$)). "Alkoxy" means an alkyl group that is linked via an oxygen (i.e., alkyl-O—), for example methoxy, ethoxy, and sec-butyloxy groups. "Alkylene" means a straight or branched chain, saturated, divalent aliphatic hydrocarbon group (e.g., methylene (—CH$_2$—) or, propylene (—(CH$_2$)$_3$—)). "Cycloalkylene" means a divalent cyclic alkylene group, —C$_n$H$_{2n-x}$, wherein x is the number of hydrogens replaced by cyclization(s). "Cycloalkenyl" means a monovalent group having one or more rings and one or more carbon-carbon double bonds in the ring, wherein all ring members are carbon (e.g., cyclopentyl and cyclohexyl). "Aryl" means an aromatic hydrocarbon group containing the specified number of carbon atoms, such as phenyl, tropone, indanyl, or naphthyl. "Arylene" means a divalent aryl group. "Alkylarylene" means an arylene group substituted with an alkyl group. "Arylalkylene" means an alkylene group substituted with an aryl group (e.g., benzyl). The prefix "halo" means a group or compound including one more of a fluoro, chloro, bromo, or iodo substituent. A combination of different halo groups (e.g., bromo and fluoro), or only chloro groups can be present. The prefix "hetero" means that the compound or group includes at least one ring member that is a heteroatom (e.g., 1, 2, or 3 heteroatom(s)), wherein the heteroatom(s) is each independently N, O, S, Si, or P. "Substituted" means that the compound or group is substituted with at least one (e.g., 1, 2, 3, or 4) substituents that can each independently be a C$_{1-9}$ alkoxy, a C$_{1-9}$ haloalkoxy, a nitro (—NO$_2$), a cyano (—CN), a C$_{1-6}$ alkyl sulfonyl (—S(=O)$_2$-alkyl), a C$_{6-12}$ aryl sulfonyl (—S(=O)$_2$-aryl) a thiol (—SH), a thiocyano (—SCN), a tosyl (CH$_3$C$_6$H$_4$SO$_2$—), a C$_{3-12}$ cycloalkyl, a C$_{2-12}$ alkenyl, a C$_{5-12}$ cycloalkenyl, a C$_{6-12}$ aryl, a C$_{7-13}$ arylalkylene, a C$_{4-12}$ heterocycloalkyl, and a C$_{3-12}$ heteroaryl instead of hydrogen, provided that the substituted atom's normal valence is not exceeded. The number of carbon atoms indicated in a group is exclusive of any substituents. For example —CH$_2$CH$_2$CN is a C$_2$ alkyl group substituted with a nitrile.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

What is claimed is:

1. A method of making alkyl tribenzoates comprising:
   combining a phenyl tricarboxylic acid or chemical equivalent thereof with greater than or equal to 3.5 molar equivalents of a C$_4$-C$_{18}$ alkyl alcohol, based on the amount of phenyl tricarboxylic acid or chemical equivalent thereof, in the presence of 0.05 to 0.20 mol % of a titanium tetra-alkoxide catalyst, based on the total moles of phenyl tricarboxylic acid or chemical equivalent, at a temperature greater than 210° C. to form a reaction mixture having an acid value less than or equal to 0.5 as determined according to ASTM D1045.

2. The method of claim 1 further comprising neutralizing the reaction mixture with an aqueous caustic solution, and purging the neutralized reaction mixture with carbon dioxide.

3. The method of claim 2, further comprising distilling residual C$_4$-C$_{18}$ alkanol from the reaction mixture either prior to purging, subsequent to purging or both.

4. The method of claim 3, further comprising filtering the distilled reaction mixture after purging through celite, contacting the filtered reaction mixture with charcoal; and filtering the charcoal containing mixture to produce a product having an acid value less than 0.1 and an APHA color value less than 30 as determined according to ASTM D1045.

5. The method of claim 1, wherein the phenyl tricarboxylic acid or chemical equivalent thereof comprises trimellitic anhydride.

6. The method of any of claim 1, wherein the C$_4$-C$_{18}$ alkyl alcohol comprises 2-ethylhexyl alcohol.

7. The method of claim 1, wherein the titanium tetra-alkoxide catalyst comprises titanium tetra-isopropoxide catalyst.

8. The method of claim 1, wherein the reaction mixture has an acid value less than or equal to 0.3.

9. The method of claim 1, wherein the C$_4$-C$_{18}$ alkyl alcohol is present in an amount of 3.5 to 4.5 molar equivalents, based on the amount of phenyl tricarboxylic acid or chemical equivalent thereof.

10. The method of claim 1, wherein the temperature is less than or equal to 250° C.

11. A method of making alkyl tribenzoates comprising:
    combining a phenyl tricarboxylic acid or chemical equivalent thereof with greater than or equal to 3.5 molar equivalents of a C$_4$-C$_{18}$ alkyl alcohol in the presence of 0.05 to 0.20 mol % of a titanium tetra-isopropoxide catalyst, based on the total moles of phenyl tricarboxylic acid or chemical equivalent, at a temperature greater than 210° C. to form a reaction mixture; neutralizing the reaction mixture with an aqueous caustic solution and purging the neutralized reaction mixture with carbon dioxide; distilling any residual C$_4$-C$_{18}$ alkanol from the purged reaction mixture; filtering the distilled reaction mixture through celite; and contacting the filtered reaction mixture with charcoal to form a product having an acid value less than 0.1 and an APHA color value less than or equal to 30 both determined according to ASTM D1045.

12. The method of claim 11, further comprising distilling C$_4$-C$_{18}$ alkanol from the reaction mixture prior to neutralizing.

13. The method of claim 11, wherein the phenyl tricarboxylic acid or chemical equivalent thereof comprises trimellitic anhydride.

14. The method of claim 11, wherein the C$_4$-C$_{18}$ alkyl alcohol comprises 2-ethylhexyl alcohol.

15. A method of making alkyl tribenzoates comprising:
    combining a trimellitic acid or a trimellitic anhydride or a combination thereof with greater than or equal to 3.5 molar equivalents of a 2-ethylhexyl alcohol, based on the total moles of trimellitic acid or trimellitic anhydride or combination thereof, in the presence of 0.05 to 0.20 mol % of a titanium tetra-isopropoxide catalyst at a temperature greater than 210° C. to form a reaction mixture having an acid value less than or equal to 0.3.

16. The method of claim 15 further comprising neutralizing the reaction mixture with an aqueous caustic solution, and purging the neutralized reaction mixture with carbon dioxide.

17. The method of claim 16, further comprising distilling residual C$_4$-C$_{18}$ alkanol from the reaction mixture either prior to purging, subsequent to purging or both.

18. The method of claim 17, further comprising filtering the distilled reaction mixture after purging through celite, contacting the filtered reaction mixture with charcoal; and filtering the charcoal containing mixture to produce a product having an acid value less than 0.1 and an APHA color value less than 30 as determined according to ASTM D1045.

19. The method of claim 15, wherein the 2-ethylhexyl alcohol is present in an amount of 3.5 to 4.5 molar equivalents, based on the total moles of trimellitic acid or trimellitic anhydride or combination thereof.

20. The method of claim 15, wherein the temperature is less than or equal to 250° C.

\* \* \* \* \*